United States Patent [19]

Lacefield et al.

[11] 4,452,745

[45] Jun. 5, 1984

[54] 9-AMINOALKYLFLUORENES

[75] Inventors: William B. Lacefield, Indianapolis; Richard L. Simon, Greenwood, both of Ind.

[73] Assignee: Eli Lilly and Company, Indianapolis, Ind.

[21] Appl. No.: 426,491

[22] Filed: Sep. 29, 1982

Related U.S. Application Data

[60] Division of Ser. No. 232,281, Feb. 6, 1981, Pat. No. 4,382,093, which is a division of Ser. No. 141,228, Apr. 17, 1980, Pat. No. 4,277,495, which is a continuation-in-part of Ser. No. 19,533, Mar. 12, 1979, abandoned.

[51] Int. Cl.$^3$ .................... C07C 121/78; C07C 87/28; C07C 103/28
[52] U.S. Cl. ............................... 260/465 E; 544/154; 544/380; 546/203; 546/204; 564/164; 564/285; 564/355
[58] Field of Search .................... 260/465 E; 564/164, 564/285, 355; 544/154, 380; 546/203, 204

[56] References Cited

U.S. PATENT DOCUMENTS

| 3,476,545 | 11/1969 | Mohr | 71/76 |
|---|---|---|---|
| 3,660,485 | 5/1972 | Cusic | 260/558 H |
| 3,843,657 | 10/1974 | Lowrie | 260/558 |
| 4,001,328 | 1/1977 | Molloy | 260/567.6 M |
| 4,197,313 | 4/1980 | Lacefield | 424/304 |
| 4,277,471 | 7/1981 | Lacefield | 424/248.4 |
| 4,277,495 | 7/1981 | Lacefield | 424/309 |

FOREIGN PATENT DOCUMENTS 960758  6/1964  United Kingdom .

OTHER PUBLICATIONS

Wheatley et al., J. Org. Chem. 19, 794–801 (1954).
Libman et al., Chem. Abs. 59, 561 (1963).
Miocque et al., Chem. Abs. 61, 8267 (1964).
Boehringer et al., Chem. Abs. 59, 13906–13907 (1963).
Boehringer et al., Chem. Abs. 70, 37664 (1969).
Bonvicino et al., Chem. Abs. 55, 27340–27343 (1961).
Boehringer, Chem. Abs. 64, 14199 (1966).
Gautier et al., Bull Soc. Chim. Fr., 11, 3162 (1965).
Boehringer, Chem. Abs. 70, 3442 (1969).

*Primary Examiner*—Dolph H. Torrence
*Attorney, Agent, or Firm*—Charles W. Ashbrook; Arthur R. Whale

[57] ABSTRACT

Fluorenes bearing a 9-aminoalkyl substituent are useful antiarrhythmic agents. Pharmaceutical formulations containing such compounds are provided, as well as a method of treatment.

29 Claims, No Drawings

9-AMINOALKYLFLUORENES

CROSS-REFERENCE TO RELATED APPLICATIONS

This application is a division of application Ser. No. 232,281, filed Feb. 6, 1981, now U.S. Pat. No. 4,382,093, which is a division of Ser. No. 141,228, filed Apr. 17, 1980, now U.S. Pat. No. 4,227,495, which is a continuation-in-part of Ser. No. B 019,533, filed Mar. 12, 1979, now abandoned.

BACKGROUND OF THE INVENTION

This invention concerns fluorenes which bear an aminoalkyl substituent at the 9-position. Such compounds are useful antiarrhythmic agents.

Substituted flourenes are well known in the art. For example, 9-hydroxy-9-dimethylaminoethylfluorene and 9-hydroxy-9-dimethylaminopropylfluorene are described in *Comp. Rend.*, 259(2), 408–10(1964), cf. *Chem Abst.* Vol. 61, 8267b (1964). Similarly, 9-hydroxy-9-(3-tertiary aminopropyl)fluorenes are disclosed as intermediates by Stach in British Pat. No. 960,758. Lowrie, in U.S. Pat. No. 3,843,657, discloses 9-dialkylaminoalkylfluorene-9-carboxamides, wherein the carboxamide nitrogen is required to be part of an alkylene diamine moiety. Such compounds allegedly are useful as antibacterial and antifungal agents. Cusic, in U.S. Pat. No. 3,660,485, discloses 9-dialkylaminoalkylfluorene-9-carboxylic acid hydrazides which are said to have antibacterial and antifungal activity, as well as being useful as antiarrhythmic agents.

SUMMARY OF THE INVENTION

This invention concerns new fluorenes which bear an aminoalkyl substituent at the 9-position. Such compounds are antiarrhythmic agents. The invention is more particularly directed to 9-aminoalkylfluorenes defined by the formula

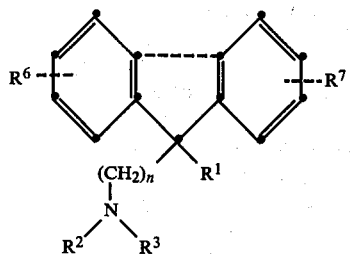

wherein:
$R^1$ is hydroxy, cyano, or $CONR^4R^5$ in which $R^4$ and $R^5$ independently are hydrogen or $C_1$–$C_6$ alkyl;
$R^2$ and $R^3$ independently are hydrogen, $C_1$–$C_6$ alkyl, $CH_2C_2$–$C_5$ alkenyl, phenyl-$C_1$–$C_3$ alkyl, or taken together with the nitrogen to which they are attached are a cyclic group of the formula

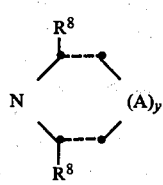

in which $R^8$ is hydrogen or $C_1$–$C_4$ alkyl; A is $CH_2$, O or NH; and y is zero or one; provided that $R^2$ is hydrogen when $R^1$ is hydroxy;
n is 3, 4 or 5; and $R^6$ and $R^7$ independently are hydrogen, $C_1$–$C_4$ alkyl or halogen.

Preferred compounds of the invention have the above formula wherein:
$R^1$ is hydroxy, cyano, or $CONR^4R^5$ in which $R^4$ and $R^5$ independently are hydrogen or $C_1$–$C_6$ alkyl;
n is 3 or 4;
$R^2$ and $R^3$ independently are hydrogen, $C_1$–$C_6$ alkyl, $CH_2C_2$–$C_5$ alkenyl, phenyl-$C_1$–$C_3$ alkyl, or taken together are $C_4$–$C_5$ alkylene or $-CH_2CH_2OCH_2CH_2-$;
and $R^6$ and $R^7$ are hydrogen.

Additionally preferred compounds of the invention are those defined by the above formula wherein n is 3. Further preferred compounds are those wherein $R^1$ is cyano or $CONR^4R^5$. The most preferred compounds have the above formula wherein n is 3, $R^1$ is $CONH_2$, $R^2$ is hydrogen, $R^3$ is $C_1$–$C_6$ alkyl and $R^6$ and $R^7$ both are hydrogen. $R^3$ ideally is $C_1$–$C_3$ alkyl. An especially important compound provided is 9-(3-isopropylaminopropyl)-9-aminocarbonylfluorene.

Also included within this invention are the pharmaceutically acceptable acid addition salts of the amine bases defined by the above formula, as well as the quaternary ammonium salts formed with $C_1$–$C_6$ alkyl alkylating agents when $R^2$ and $R^3$ both are other than hydrogen.

This invention also provides pharmaceutical formulations which are useful in the treatment of subjects in need of antiarrhythmic care which comprise a pharmaceutically acceptable carrier, adjuvant, diluent, or the like, admixed with a 9-aminoalkylfluorene antiarrhythmic agent of the formula

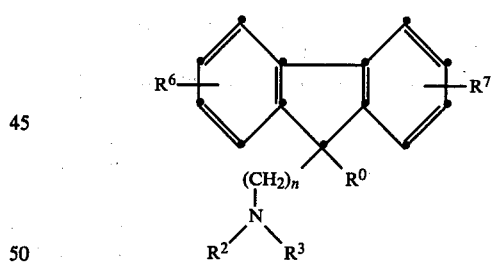

wherein $R^0$ is $R^1$ as defined above, as well as $COOR^9$ wherein $R^9$ is hydrogen or $C_1$–$C_4$ alkyl; and n, $R^2$, $R^3$, $R^6$ and $R^7$ are as defined above, and the pharmaceutically acceptable salts thereof.

Preferred formulations according to this invention are those wherein the active ingredient is a compound of the above formula in which:
$R^0$ is $R^1$, and is especially cyano or $CONR^4R^5$;
n is 3;
$R^2$ is hydrogen;
$R^3$ is $C_1$–$C_6$ alkyl; and
$R^6$ and $R^7$ both are hydrogen.

In yet another embodiment of the invention there is provided a method for treating cardiac arrhythmias comprising administering to a subject an antiarrhythmic amount of a compound of the formula

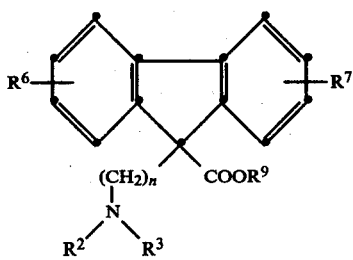

wherein: $R^2$, $R^3$, $R^6$, $R^7$, $R^8$ $R^9$ and n have the above-defined meanings. Such compounds are disclosed as chemical intermediates by Cusic et al. in U.S. Pat. No. 3,660,485.

DETAILED DESCRIPTION OF THE INVENTION

As used herein, the term "$C_1$–$C_6$ alkyl" refers to both straight and branched chain groups such as methyl, ethyl, n-propyl, iso-propyl, n-butyl, iso-butyl, tert-butyl, n-pentyl, iso-pentyl, n-hexyl, 2-methylbutyl, 2-ethylbutyl, and the like. Preferred alkyl groups are $C_1$–$C_3$ alkyl groups such as methyl, ethyl and iso-propyl.

The term "$CH_2C_2$–$C_5$ alkenyl" includes unsaturated carbon chains such as allyl, 2-butenyl, 2-pentenyl, 2-hexenyl, 2-methyl-2-pentenyl, 3-hexenyl, 4-methyl-2-pentenyl, and related alkenyl groups. Typical examples of phenyl-$C_1$–$C_3$ alkyl groups include benzyl, 2-phenethyl and 3-phenylpropyl.

$R^2$ and $R^3$ can be taken together with the nitrogen atom to which they are attached to complete a heterocyclic ring. Examples of such rings include pyrrolidino, piperidino, piperazino, morpholino, 2,6-dimethylpiperidino, 2,6-diethylpiperidino, 2,5-dimethylpyrrolidino, and the like.

Examples of "halogen" as used herein include fluorine, chlorine, bromine and iodine.

The 9-aminoalkylfluorenes of this invention can be prepared by a variety of methods. One method for preparing the 9-aminoalkyl-9-hydroxyfluorenes of the invention comprises reacting a fluoren-9-one with an aminoalkyne in the presence of a strong base to provide the corresponding 9-aminoalkynyl-9-hydroxyfluorene, which upon hydrogenation affords the corresponding 9-aminoalkyl-9-hydroxyfluorene of the invention. Such process can be illustrated as follows:

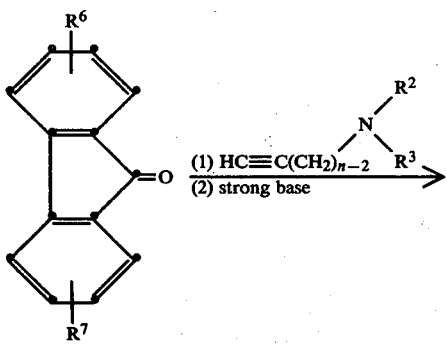

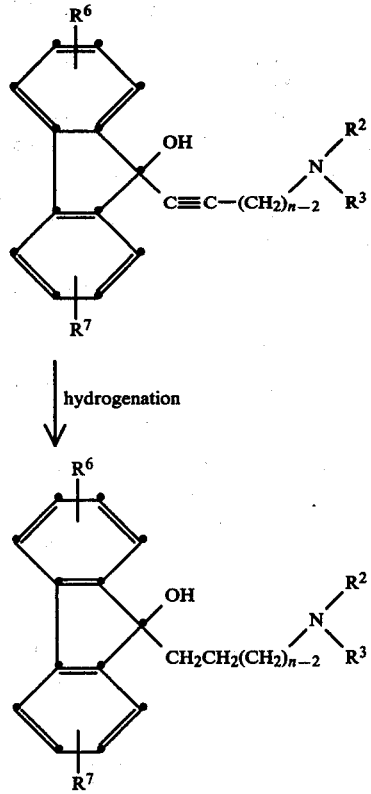

Fluoren-9-ones which can be utilized include fluoren-9-one, 1,8-dimethylfluoren-9-one, 2,7-dibromofluoren-9-one, 3-ethyl-8-n-butylfluoren-9-one, and the like.

The alkynylation of a fluoren-9-one is carried out by combining approximately equimolar amounts of a strong base with an aminoalkyne. Strong bases commonly utilized include alkali metal lower alkyl metalides such as methyl lithium, n-butyl lithium, methyl sodium; alkali metal amides such as sodium amide, potassium amide and lithium diisopropylamide, as well as alkali metal hydrides such as sodium and potassium hydride. Examples of aminoalkynes commonly used include 3-methylaminopropyne, 4-ethylaminobutyne, 5-isopropylaminopentyne, 3-isopropylaminopropyne, 3-n-pentylaminopropyne, 3-tert-butylaminopropyne and the like. Typically the strong base and aminoalkyne are combined in an unreactive organic solvent such as diethyl ether, tetrahydrofuran, toluene, 1,2-dimethoxyethane, xylene, or the like, and stirred for about one hour at a reduced temperature of about −40° to about −80° C. The fluoren-9-one is then added to the cold reaction mixture and stirring is continued at sub-zero temperature for about one hour, after which time the mixture is heated to about 30° to 80° C. and stirred for an additional eight to sixteen hours. After the reaction is complete, the mixture is diluted with water, thus decomposing any remaining strong base, and then the product is extracted into a suitable water immiscible solvent such as diethyl ether or benzene. Removal of such solvent, for instance by evaporation under reduced pressure, provides the corresponding 9-aminoalkynyl-9-hydroxyfluorene. Such intermediate can be further purified if desired by routine methods such as chromatography, distillation, salt formation, or the like.

The 9-aminoalkynyl-9-hydroxyfluorene thus obtained can be converted to the corresponding 9-aminoalkyl-9-hydroxyfluorene of this invention by hydrogenation in the presence of a catalyst such as platinum or palladium on carbon. Such hydrogenation reactions generally are carried out in a solvent such as ethyl acetate or ethanol, and normally are complete after about two to ten hours when carried out at a hydrogen pressure of about 60 psi and at a temperature of about −25° to about 110° C. The product, a 9-aminoalkyl-9-hydroxyfluorene of this invention, can be isolated by simply filtering off the catalyst and removing the reaction solvent, for example by evaporation. The product can be further purified if needed by routine methods such as distillation or salt formation.

The 9-aminoalkyl-9-hydroxyfluorenes can alternatively be prepared by reaction of a fluoren-9-one with an aminoalkyl Grignard reagent. For example, reaction of fluoren-9-one with a Grignard reagent such as 3-isopropylaminopropyl magnesium chloride affords, after a standard work-up and isolation, the corresponding 9-aminoalkyl-9-hydroxyfluorene, namely 9-(3-isopropylaminopropyl)-9-hydroxyfluorene.

The compounds of this invention wherein $R^1$ is cyano, i.e. the 9-aminoalkyl-9-cyanofluorenes, can be prepared by alkylation of a 9-cyanofluorene with an aminoalkyl alkylating agent. Typical alkylating agents include aminoalkyl halides such as 3-methylaminopropyl chloride, 3-isopropylaminopropyl bromide, 3-diethylaminopropyl iodide, 5-ethylisobutylaminopentyl chloride, 5-methylaminopentyl bromide, 4-isopropylaminobutyl iodide and 3-di-n-hexylaminopropyl bromide. Typical 9-cyanofluorene starting materials include 2-bromo-9-cyanofluorene, 3-n-propyl-9-cyanofluorene, 2,7-difluoro-9-cyanofluorene, and the like.

The alkylation reaction is carried out by commingling approximately equimolar quantities of a 9-cyanofluorene and an aminoalkyl alkylating agent in a suitable unreactive solvent such as toluene or benzene and in the presence of about an equimolar quantity of strong base such as sodium amide, lithium amide, n-butyl lithium, sodium methoxide, potassium tert-butoxide or the like. The alkylation normally is substantially complete after about ten to twenty hours when carried out at a temperature from about 30° to about 150° C. The alkylated fluorene, i.e. the 9-aminoalkyl-9-cyanofluorene, can be isolated by simply diluting the reaction mixture with water and then extracting the product therefrom into a water immiscible solvent such as benzene, diethyl ether or the like. Removal of the solvent then provides the 9-cyanofluorene of this invention, which can be further purified if desired by routine methods, including distillation and salt formation.

The 9-aminoalkyl-9-cyanofluorenes thus prepared are valuable antiarrhythmic agents, and additionally serve as intermediates leading to the primary 9-carboxamides of this invention, i.e. compounds of the above formula wherein $R^1$ is $CONR^4R^5$ and $R^4$ and $R^5$ both are hydrogen. The 9-aminoalkyl-9-cyanofluorenes can be hydrolyzed to the corresponding primary carboxamides by reaction with any of a number of acids such as concentrated sulfuric acid, acetic acid and boron trifluoride, dry hydrogen chloride; or alternatively by reaction with hydrogen peroxide and a base such as sodium hydroxide, or with manganese dioxide in dichloromethane. A preferred hydrolysis process comprises simply heating a solution of the 9-aminoalkyl-9-cyanofluorene in sulfuric acid for about one hour at a temperature of about 90° to 100° C. The corresponding primary carboxamide that is formed is readily isolated by making the reaction mixture alkaline, for example by adding sodium hydroxide until the pH reaches about 10, and then extracting the primary carboxamide into a suitable water immiscible solvent such as diethyl ether or benzene. Evaporation of the organic solvent then provides the desired 9-aminoalkyl-9-aminocarbonylfluorene. Such compound can be further purified if desired by crystallization or salt formation.

Compounds of this invention wherein $R^1$ is $CONR^4R^5$ and one or both of $R^4$ and $R^5$ are alkyl can be prepared by reacting a 9-aminoalkyl-9-fluorenyl carboxylic acid halide or lower alkyl ester with a primary or secondary amine of the formula $HNR^4R^5$. For example, a fluorenyl carboxylic acid such as 9-(3-N-benzyl-N-isopropylaminopropyl)-9-hydroxycarbonylfluorene can be reacted with oxalyl chloride to give the corresponding acid chloride, namely 9-(3-N-benzyl-N-isopropylaminopropyl)-9-chlorocarbonylfluorene. Reaction of the latter compound with an amine such as methylamine affords the corresponding methyl substituted carboxamide, namely 9-(3-N-benzyl-N-isopropylaminopropyl)-9-methylaminocarbonylfluorene. The substituted carboxamides of the invention can alternatively be prepared by reacting a substituted amine with an ester of a fluorene 9-carboxylic acid. This method is similar to that described in U.S. Pat. No. 3,660,485. For example, an ester such as 9-(3-ethylaminopropyl)-9-methoxycarbonylfluorene can be reacted with an excess of an amine such as isopropylamine in a suitable solvent such as toluene to provide the corresponding carboxamide, namely 9-(3-ethylaminopropyl)-9-isopropylaminocarbonylfluorene.

The compounds comprehended by this invention alternatively can be prepared by first synthesizing a 9-(unsubstituted aminoalkyl)fluorene, and then alkylating such compound with the desired $R^2$ or $R^3$ alkylating agents. Such process is depicted by the following scheme:

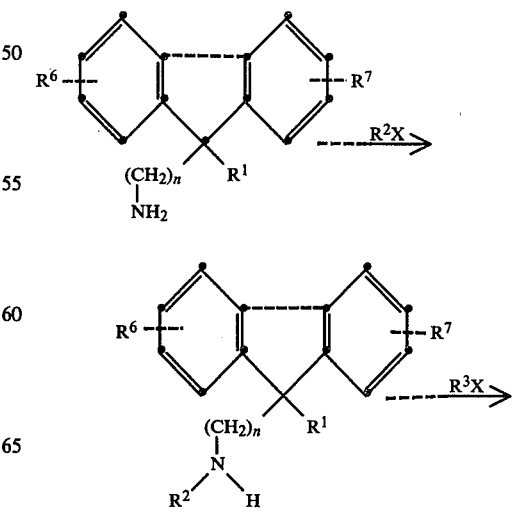

-continued

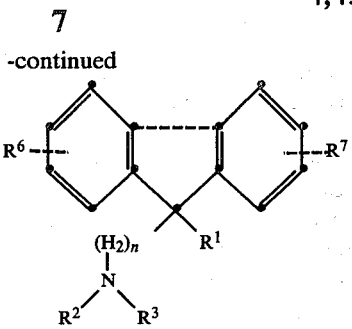

in which n, $R^1$, $R^2$, $R^3$, $R^6$ and $R^7$ have the above-defined meanings, and X is a leaving group such as halogen. Alkylation of primary amines is well known in the art and typically is carried out by combining an amine and an alkylating agent in the presence of a base such as sodium bicarbonate or triethylamine to act as an acid scavenger. The reactions normally are carried out in organic solvents such as toluene, dimethylsulfoxide, ethanol, methanol or the like. As an illustration of the process, a fluorene derivative such as 9-(3-aminopropyl)-9-cyanofluorene can be mixed with about an equimolar quantity of an alkylating agent such as allyl bromide in a solvent such as benzene and in the presence of triethylamine. The reaction mixture can be heated to about 50° C. and stirred for about two hours to provide the corresponding alkylated aminopropylfluorene derivative wherein $R^2$ is allyl, namely 9-(3-allylaminopropyl)-9-cyanofluorene. Further alkylation of such secondary amine with yet a different alkylating agent, for example $R^3X$ wherein $R^3$ is benzyl, affords the corresponding tertiary amine, namely 9-(3-N-allyl-N-benzylaminopropyl)-9-cyanofluorene. It should be at once recognized that hydrolysis of the cyano moiety as hereinabove discussed provides the corresponding 9-carboxamide derivative.

A similar yet alternative process involves, as a first step, reaction of a fluorene such as a 9-cyanofluorene with a strong base such as sodium amide, and an alkylene dihalide such as 1,3-dichloropropane or 1,5-dibromopentane, to provide the corresponding 9-cyano-9-(ω-haloalkyl)fluorene, which is then condensed with an amine of the formula $HNR^2R^3$ to give a compound of the invention.

Still another method for preparing compounds of the invention comprises reductive amination of a 9-cyanoalkylfluorene by reaction with an amine of the formula $HNR^2R^3$ in the presence of hydrogen and a hydrogenation catalyst. Such method is particularly preferred for the preparation of 9-cyano and 9-aminocarbonylfluorene derivatives which bear an aminopropyl moiety as the 9-position. For example, a 9-substituted fluorene such as 9-aminocarbonylfluorene can be reacted with a cyanoalkene such as acrylonitrile in the presence of a base such as sodium hydride or Triton B to provide the corresponding 9-aminocarbonyl-9-(ω-cyanoalkyl)fluorene, for instance 9-aminocarbonyl-9-(2-cyanoethyl)fluorene. The latter compound can then be reacted with an amine, for instance isopropylamine or the like, in the presence of hydrogen and a catalyst such as palladium on carbon. The hydrogenation generally is carried out at a pressure of about 50 to about 2000 psi and at a temperature of about 50° to about 100° C. to provide the 9-aminoalkylfluorene of the invention. Isolation and purification of the product can be accomplished by routine procedures. Simple hydrogenation of a 9-(ω-cyanoalkyl)fluorene in the presence of a solvent such as acetic acid provides the corresponding 9-(ω-unsubstituted aminoalkyl)fluorene.

Various of the compounds provided by this invention are useful as intermediates in addition to being valuable antiarrhythmic agents. For example, the N-benzyl aminoalkylfluorenes of the above formula can be de-benzylated by hydrogenation in the presence of a catalyst such as palladium. Similarly, N-methyl aminoalkylfluorenes can be de-methylated. For example, a compound such as 9-(4-N-n-propyl-N-methylaminobutyl)-9-cyanofluorene can be reacted with a haloformate such as phenyl chloroformate to form a carbonate, which when reacted with alkali is hydrolyzed to the corresponding secondary amine, namely 9-(4-N-n-propylaminobutyl)-9-cyanofluorene. The latter compound is a potent antiarrhythmic agent, and additionally can be utilized as an intermediate in the preparation of other antiarrhythmic agents. For instance, normal alkylation with an alkylating agent such as 3-phenylpropyl bromide affords 9-[4-N-(3-phenylpropyl)-N-n-propylaminobutyl]-9-cyanofluorene.

The compounds provided by this invention are basic in nature by virtue of the nitrogen atom of the 9-aminoalkyl substituent. Such compounds consequently react with a number of acids to form salts. This invention additionally provides pharmaceutically acceptable acid addition salts of the compounds defined by the above general formula, which are those acid addition salts which add no substantial toxicity to the free base from which they are derived. The pharmaceutically acceptable acid addition salts thus provided are prepared by reacting a 9-aminoalkylfluorene of this invention with any of a number of acids. Inorganic acids commonly utilized include hydrochloric, hydrobromic, phosphoric, sulfuric, nitric, perchloric and similar acids. Organic acids frequently utilized to form pharmaceutically acceptable acid addition salts include acetic, succinic, maleic, methanesulfonic, citric, fumaric, para-toluenesulfonic, and related organic acids.

Additionally provided herein are the lower alkyl quaternary ammonium salts which can be prepared when $R^2$ and $R^3$ in the above general formula both are other than hydrogen. For example, normal alkylation of a tertiary amine such as 9-(3-N-methyl-N-isopropylaminopropyl)-9-aminocarbonylfluorene by reaction with a lower $C_1$–$C_6$ alkylating agent such as methyl chloride, ethyl bromide, n-butyl iodide, isohexyl bromide, or the like, affords the corresponding quaternary ammonium salt. Such salts characteristically are highly crystalline solids and can be purified by recrystallization from solvents such as ethanol, water, and the like.

The following compounds are representative of those comprehended by this invention.
9-(5-methylaminopentyl)-9-hydroxyfluorene;
9-(3-isopropylaminopropyl)-9-hydroxyfluorene;
9-(4-isopropylaminobutyl)-9-hydroxyfluorene;
9-(3-n-hexylaminopropyl)-9-hydroxy-3,7-diethylfluorene;
9-(3-tert-butylaminopropyl)-9-hydroxy-5-bromofluorene hydrobromide;
9-(5-allylaminopentyl)-9-hydroxyfluorene;
9-[3-(2-butenylamino)propyl]-9-hydroxyfluorene;
9-[4-(2-phenylethylamino)butyl]-9-hydroxy-3-iodofluorene;
9-(4-ethylaminobutyl)-9-cyanofluorene;
9-(5-isopropylaminopentyl)-9-cyanofluorene;
9-(3-isopropylaminopropyl)-9-cyanofluorene;

9-(3-benzylaminopropyl)-9-cyanofluorene;
9-(4-allylaminobutyl)-9-cyanofluorene;
9-[3-(3-phenylpropylamino)propyl]-9-cyano-2,7-dichlorofluorene;
9-(4-N-isopropyl-N-ethylaminobutyl)-9-cyanofluorene;
9-(3-N,N-diisopropylaminopropyl)-9-cyano-1,8-dimethylfluorene;
9-[3-N-isopropyl-N-(2-phenylethyl)aminopropyl]-9-cyanofluorene;
9-(2-tert-butylaminoethyl)-9-cyanofluorene;
9-[3-(3-hexenylamino)propyl]-9-cyanofluorene;
9-(4-diethylaminobutyl)-9-cyanofluorene;
9-(3-isopropylaminopropyl)-9-cyanofluorene hydrosulfate;
9-(3-dibenzylaminopropyl)-9-cyanofluorene ethyl iodide;
9-(5-n-propylaminopentyl)-9-aminocarbonyl-3-ethylfluorene;
9-(4-benzylaminobutyl)-9-aminocarbonylfluorene;
9-(3-n-pentylaminopropyl)-9-aminocarbonyl-4-bromofluorene;
9-(3-isopropylaminopropyl)-9-aminocarbonylfluorene hydrophosphate;
9-(3-N-methyl-N-tert-butylaminopropyl)-9-aminocarbonylfluorene;
9-[4-(2-hexenylamino)butyl]-9-aminocarbonylfluorene;
9-[3-N-(2-phenylethyl)-N-isobutylaminopropyl]-9-aminocarbonylfluorene;
9-(3-N,N-di-n-hexylaminopropyl)-9-aminocarbonylfluorene;
9-[3-N-(2-methylpentyl)-N-ethylaminopropyl]-9-aminocarbonylfluorene;
9-(3-N-benzyl-N-isobutylaminopropyl)-9-aminocarbonylfluorene n-propyl iodide;
9-(3-isopropylaminopropyl)-9-aminocarbonylfluorene hydroacetate;
9-(3-isopropylaminopropyl)-9-methylaminocarbonylfluorene;
9-(4-diethylaminobutyl)-9-dimethylaminocarbonylfluorene;
9-(5-tert-butylaminopentyl)-9-isopropylaminocarbonylfluorene;
9-(3-isopropylaminopropyl)-9-isopropylaminocarbonylfluorene hydrochloride;
9-(4-benzylaminobutyl)-9-di-n-butylaminocarbonylfluorene;
9-(3-allylaminopropyl)-9-n-hexylaminocarbonylfluorene;
9-(4-morpholinobutyl)-9-aminocarbonylfluorene;
9-(5-pyrrolidinopentyl)-9-aminocarbonylfluorene;
9-(3-piperidinopropyl)-9-cyanofluorene;
9-(3-piperazinopropyl)-9-ethylaminocarbonylfluorene;
9-(3-aminopropyl)-9-isopropylaminocarbonylfluorene;
9-(3-diisopropylaminopropyl)-9-diisopropylaminocarbonylfluorene methiodide; and
9-[3-N-(2-butenyl)-N-(2-hexenyl)aminopropyl]-9-aminocarbonylfluorene.

The 9-aminoalkylfluorenes provided by this invention are useful as antiarrhythmic agents. Such utility has been determined by evaluating representative compounds of the invention in biological assays designed to measure antiarrhythmic activity. One such assay comprises administering a compound of unknown biological activity to a dog suffering from an experimentally induced cardiac arrhythmia, and observing whether or not the compound effects a conversion of the arrhythmia to a normal sinus rhythm, and if so, for how long the conversion persists.

In a typical experiment to determine the activity of the compounds of this invention, one or more mongrel dogs of either sex were anesthetized with sodium pentobarbital. A 23 gauge Butterfly infusion needle was placed in the radial vein for the introduction into the dog of sufficient ouabain to induce an arrhythmia, and for the introduction into the dog of the test compound. Each dog was continuously monitored throughout the experiment by electrocardiogram. After the ouabain induced cardiac arrhythmia had continued for thirty minutes, a compound of this invention was administered via the Butterfly infusion needle at the rate of 200 μg per kilogram of dog body weight per minute. If the arrhythmia was not converted to a normal sinus rhythm within ten minutes from the initial administration of test compound, as observed by electrocardiogram, the rate of infusion of test compound was increased to 500 μg per kilogram per minute. The amount of test compound required to convert an arrhythmia to normal rhythm was recorded as the "converting dose". Following the complete administration of test compound to the dog, the dog's heart was monitored by electrocardiogram until such time that an arrhythmia returned to the dog's heart, or for a maximum time of two hours, at which time the experiment was terminated. The duration of normal rhythm was recorded in minutes.

The results of several experiments are set out in the following table. Most of the compounds were evaluated more than once, as indicated in the "No. of Dogs" column. The average converting dose is given in mg. per kilogram of animal body weight. Average duration of conversion is recorded in minutes.

| $R^1$ | $R^2$ | $R^3$ | No. of dogs | Converting dose mg/kg | Duration minutes |
|---|---|---|---|---|---|
| CONH$_2$ | H | i-Pr | 3 | 0.7 | 120 |
| OH | H | i-Pr | 4 | 2.1 | 104 |
| CONH$_2$ | CH$_3$ | CH$_3$ | 1 | 3.2 | 80 |
| OH | H | CH$_2$–⌬ | 2 | 1.9 | 18 |

In another biological assay, known in the art as the canine HIS bundle electrogram, the effects of antiarrhythmic agents on conduction intervals and refractory periods in various regions of the heart are determined. When 9-(3-isopropylaminopropyl)-9-aminocarbonylfluorene hydrochloride was compared to the antiarrhythmic agent aprindine in the canine HIS bundle electrogram, it proved to be at least twice as potent in prolonging conduction intervals and refractory periods.

The compounds of this invention can be employed in combatting cardiac arrhythmias in animals by administering an antiarrhythmic amount of one or more of the aminoalkylfluorenes to an animal. The compounds are effective as antiarrhythmic agents when administered internally to an animal so as to introduce the compound into the animal's cardiovascular system. Parenteral administration of the compounds can be accomplished by intraperitoneal, subcutaneous or intravenous injection. The compounds alternatively can be administered orally in the form of tablets, capsules, elixirs, syrups, buccal seals and the like. The aminoalkylfluorenes of this invention have good antiarrhythmic activity both therapeutically, for instance when administered to an animal suffereing from an arrhythmia an in need of treatment, and prophylactically when administered to an animal suspected of developing an arrhythmia, thereby protecting the animal against the occurrence or recurrence of arrhythmias.

In a further embodiment of this invention there is provided a method of treatment of cardiac arrhythmias which comprises administering to an animal in need of treatment an antiarrhythmic amount of a compound of the formula

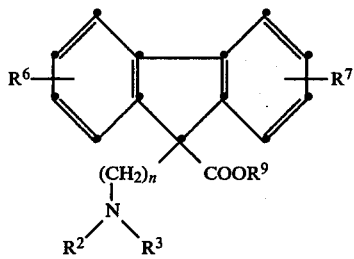

wherein $R^2$, $R^3$, n, $R^6$, $R^7$ and $R^9$ are as above defined. A preferred method employs compounds in which n is 3, $R^6$ and $R^7$ both are hydrogen and $R^9$ is $C_1$-$C_4$ alkyl such as methyl or ethyl. A typical method of treatment employs a compound such as 9-(3-isopropylaminopropyl)-9-ethoxycarbonylfluorene, which when evaluated according to the procedure described above in two dogs having ouabain induced arrhythmias demonstrated an average converting dose of 2.8 mg./kg. with an average duration of conversion of 42 minutes.

The compounds provided herein are preferably utilized in the form of pharmaceutical formulations. The invention therefore provides as another embodiment pharmaceutical formulations comprising a suitable pharmaceutical carrier, diluent, or excipient admixed with a 9-aminoalkylfluorene antiarrhythmic agent of the formula

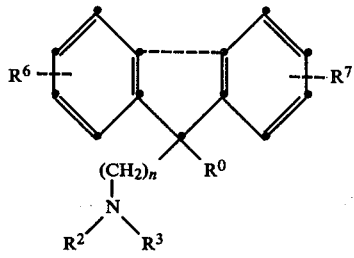

wherein:
$R^0$ is hydroxy, cyano, $CONR^4R^5$ or $COOR^9$, in which $R^4$ and $R^5$ independently are hydrogen or $C_1$-$C_6$ alkyl, and $R^9$ is hydrogen or $C_1$-$C_4$ alkyl;
n is 3, 4 or 5;
$R^2$ and $R^3$ independently are hydrogen, $C_1$-$C_6$ alkyl, $CH_2C_2$-$C_5$ alkenyl, phenyl-$C_1$-$C_3$ alkyl; or together with the nitrogen to which they are attached are a cyclic group of the formula

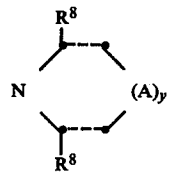

wherein:
$R^8$ is hydrogen or $C_1$-$C_4$ alkyl;
A is $CH_2$, O or NH; and
y is zero or one; and provided that $R^2$ is hydrogen when $R^0$ is hydroxy;
$R^6$ and $R^7$ independently are hydrogen, $C_1$-$C_4$ alkyl or halogen; and the pharmaceutically-acceptable salts thereof.

Preferred pharmaceutical formulations employ a compound of the above formula wherein $R^0$ is hydroxy, cyano or $CONR^4R^5$, n is 3, $R^2$ is hydrogen, $R^3$ is $C_1$-$C_6$ alkyl and $R^6$ and $R^7$ both are hydrogen.

The formulations provided herein ideally contain from about 1 to about 50 percent by weight of an aminoalkylfluorene in combination with a suitable diluent, excipient or carrier therefor. Diluents commonly utilized in formulating the compounds in solid form suitable for oral administration include starch, lactose, gelatin, silica gel, rice flour, carboxymethyl cellulose and the like. Carriers employed in liquid formulations suitable for parenteral administration via the intravenous, intramuscular, or subcutaneous routes include water, saline, glucose syrup, ethanol, corn oil and the like.

The 9-aminoalkylfluorenes of this invention can be administered to a subject suffering from an arrhythmia and in need of treatment, or to a subject suspected of developing an arrhythmia and in need of prophylactic treatment. Parenteral administration may be preferred for subjects suffering fron a life-threatening arrhythmia. Oral administration generally is preferred for maintenance or prophlylactic treatment. The compounds ideally are formulated in such a way that the effective dose of 9-aminoalkylfluorene is an amount sufficient to treat the arrhythmia. Such doses typically will be from about 0.05 to about 25 mg./kg. A typical oral dose for the treatment of a patient suffering from an arrhythmia will be, for example, from about 3.5 to about 400 mg., preferably from about 1.0 to about 200 mg., of a suitably formulated aminoalkylfluorene, for instance 9-isopropylaminopropyl-9-aminocarbonylfluorene, preferably as a pharmaceutically acceptable acid addition salt such as the hydrochloride salt. Such oral dosing may be made from 1 to about 4 times each day, or as dictated by the particular patient and condition being treated. Such compound can of course be formulated for parenteral administration, for instance by intravenous infusion. Such formulation can be prepared by dissolving about 500 mg. of the above-noted compound in a suitable diluent such as 1000 ml. of 5 percent glucose. Such solution can be infused at the rate of about 1 ml. per minute into a patient suffering from an arrhythmia.

The preparation of the aminoalkylfluorenes of this invention is more fully described in the following detailed examples. It is to be understood, however, that the examples are illustrative of the compounds embraced by this invention and are not to be construed as limiting the invention to the particular compounds or methods specifically described.

EXAMPLE 1

9-(3-Isopropylaminopropyl)-9-hydroxyfluorene

A solution of 9.0 g. of fluoren-9-one dissolved in 500 ml. of tetrahydrofuran was added dropwise over one hour to a stirred cold (−80° C.) solution of 500 ml. of tetrahydrofuran containing 9.7 g. of 3-isopropylaminopropyne and 75 ml. of a 1.6 molar tetrahydrofuran solution of n-butyl lithium. After the addition was complete, the reaction mixture was warmed to room temperature and then heated to reflux for sixteen hours. The reaction mixture was next cooled to room temperature and diluted by the dropwise addition of 200 ml. of water. The aqueous mixture was extracted several times with diethyl ether, and the ethereal extracts were combined, and the reaction product was converted to the hydrochloride salt by the addition of 300 ml. of 6N hydrochloric acid to the ethereal solution. The aqueous acid layer containing the reaction product was separated, washed once with fresh diethyl ether, and then made alkaline by the addition of 10 percent sodium hydroxide, which effected liberation of the hydrochloride salt back to the free amine. The free amine was extracted into fresh diethyl ether. The ethereal extracts were combined, washed with water and dried. Removal of the solvent by evaporation under reduced pressure then afforded 2.3 g of 9-(3-isopropylaminopropynyl)-9-hydroxyfluorene. M.P. 214°–215° C.

A solution of 2.3 g. of 9-(3-isopropylaminopropynyl)-9-hydroxyfluorene in 200 ml. of ethanol containing 3.0 g. of five percent palladium on carbon was agitated at room temperature for six hours under a hydrogen atmosphere of 60 psi. The reaction mixture then was filtered to remove the catalyst, and the filtrate was concentrated to dryness by evaporation of the solvent under reduced pressure. The solid that was thus obtained was crystallized from ethyl acetate and Skelly B to afford 1.6 g. of 9-(3-isopropylaminopropyl)-9-hydroxyfluorene. M.P. 135°–137° C.

Analysis calc. for $C_{19}H_{23}NO$: Theory: C, 81.10; H, 8.24; N, 4.98. Found: C, 81.17; H, 8.38; N, 4.72.

EXAMPLE 2

9-(3-Dimethylaminopropyl)-9-cyanofluorene

To a stirred solution of 2.6 g. of sodium amide in 200 ml. of tetrahydrofuran was added dropwise over thirty minutes a solution of 12.7 g. of 9-cyanofluorene in 300 ml. of tetrahydrofuran. The reaction mixture was next heated to reflux for three hours, and then cooled to room temperature. While the reaction mixture was being stirred at room temperature, a solution of 14.2 g. of 3-dimethylaminopropyl chloride in 500 ml. of tetrahydrofuran was added dropwise over one hour. Following complete addition, the reaction mixture was again heated to reflux and stirred for sixteen hours. After cooling the mixture to room temperature, it was added to 500 ml. of water. The product was extracted into diethyl ether, and the ethereal extracts were combined, washed with water and dried. Removal of the solvent by evaporation under reduced pressure afforded, after distillation, 2.3 g. of 9-(3-dimethylaminopropyl)-9-cyanofluorene. B.P. 195°–201° C. at 0.1 torr.

EXAMPLES 3–7

The following 9-aminoalkyl-9-cyanofluorenes were prepared by reacting 9-cyanofluorene with the appropriate aminoalkyl halide according to the procedure of Example 2.

9-(3-Piperidinopropyl)-9-cyanofluorene. B.P. 200°–208° C. at 0.18 torr.
9-(3-Diethylaminopropyl)-9-cyanofluorene. B.P. 182°–195° C. at 0.18 torr.
9-(3-N-Benzyl-N-isopropylaminopropyl)-9-cyanofluorene. B.P. 220°–245° C. at 0.18 torr.
9-(3-Isopropylaminopropyl)-9-cyanofluorene.
9-(5-Isopropylaminopentyl)-9-cyanofluorene.

EXAMPLE 8

9-(3-Isopropylaminopropyl)-9-aminocarbonylfluorene

A solution of 2.5 g. of 9-(3-isopropylaminopropyl)-9-cyanofluorene in 20 ml. of concentrated sulfuric acid and 8 ml. of water was heated at 100° C. for forty-five minutes. The reaction mixture then was added to 50 g. of ice, and 10 percent aqueous sodium hydroxide was added to pH=10. The alkaline mixture was extracted several times with diethyl ether. The ethereal extracts were combined, washed with water and dried. Removal of the solvent by evaporation under reduced pressure provided a white solid, which after crystallization from Skelly B afforded 1.2 g. of 9-(3-isopropylaminopropyl)-9-aminocarbonylfluorene.
M.P. 94°–95° C.

Analysis calc. for $C_{20}H_{24}N_2O$: Theory: C, 77.89; H, 7.84; N, 9.08. Found: C, 78.17; H, 7.65; N, 9.00.

EXAMPLES 9–12

The following fluorene carboxamides were prepared by acid hydrolysis of the corresponding fluorene nitriles according to the procedure of Example 8.

9-(3-Piperidinopropyl)-9-aminocarbonylfluorene. M.P. 155°–156.5° C.

Analysis calc. for $C_{22}H_{26}N_2O$: Theory: C, 79.00; H, 7.84; N, 8.38. Found: C, 78.73; H, 7.70; N, 8.14.

9-(3-Dimethylaminopropyl)-9-aminocarbonylfluorene. M.P. 91°–92° C.

Analysis calc. for $C_{19}H_{22}N_2O$: Theory: C, 77.52; H, 7.53; N, 9.52. Found: C, 77.51; H, 7.50; N, 9.29.

9-(3-Diethylaminopropyl)-9-aminocarbonylfluorene. M.P. 78°–79° C.

Analysis calc. for $C_{20}H_{26}N_2O$: Theory: C, 78.22; H, 8.13; N, 8.69. Found: C, 78.43; H, 8.11; N, 8.59.

9-(3-N-Benzyl-N-isopropylaminopropyl)-9-aminocarbonylfluorene.

EXAMPLE 13

9-(3-Morpholinopropyl)-9-cyanofluorene 9-cyanofluorene was reacted with sodium amide and 1,3-dichloropropane to give 9-(3-chloropropyl)-9-cyanofluorene. A solution of 10.0 g. of 9-(3-chloropropyl)-9-cyanofluorene in 200 ml. of morpholine containing 2.0 g. of potassium iodide was stirred at 160° C. for sixteen hours. After cooling the reaction mixture to room temperature, the solution was diluted with 500 ml. of water, and the aqueous mixture was extracted several times with ethylacetate. The organic extracts were combined, washed with water, and the product was extracted therefrom into 0.6N hydrochloric acid. The aqueous acid layer was separated and made alkaline by the addition of 10 percent sodium hydroxide solution. The alkaline solution was extracted with fresh ethyl acetate, and the extracts were combined, washed with water and dried. Removal of the solvent by evaporation under reduced pressure provided 9-(3-morpholinopropyl)-9-cyanofluorene.

The latter compound was dissolved in diethyl ether and the solution was saturated with hydrogen chloride. The precipitate was collected by filtration and recrystallized from diethyl ether and ethanol to afford 12.0 g. of 9-(3-morpholinopropyl)-9-cyanofluorene hydrochloride. M.P. 254°–257° C.

Analysis calc. for $C_{21}H_{23}ClN_2O$: Theory: C, 71.07; H, 6.53; N, 7.89. Found: C, 70.83; h, 6.82; N, 7.89.

EXAMPLE 14

9-(3-Isopropylaminopropyl)-9-cyanofluorene

A solution of 27.5 g. of 9-(3-N-benzyl-N-isopropylaminopropyl)-9-cyanofluorene (the compound from Example 5) in 200 ml. of ethanol containing 3.0 g. of five percent palladium on charcoal was agitated for sixteen hours at 40° C. under hydrogen at 60 psi. The reaction mixture was filtered and the solvent was evaporated from the filtrate to provide, as a gum, 23.4 g. of 9-(3-isopropylaminopropyl)-9-cyanofluorene. M+ 290; theory 290.

EXAMPLE 15

9-(3-Isopropylaminopropyl)-9-aminocarbonylfluorene hydrochloride

Hydrogen chloride was bubbled into a solution of 2.357 g. of 9-(3-isopropylaminopropyl)-9-aminocarbonylfluorene in 100 ml. of ethanol until the solution was saturated. The reaction solvent then was removed by evaporation under reduced pressure, leaving the product as an oil. The oil was crystallized from fresh ethanol and diethyl ether to give 2.145 g. of 9-(3-isopropylaminopropyl)-9-aminocarbonylfluorene hydrochloride. M.P. 203°–204° C.

Analysis calc. for $C_{20}H_{25}N_2OCl$: Theory: C, 69.65; H, 7.31; N, 8.12. Found: C, 69.94; H, 7.58; N, 8.39.

EXAMPLE 16

9-(3-N-Isopropyl-N-methylaminopropyl)-9-hydroxyfluorene methiodide

A solution of 2.7 g. of 9-(3-N-isopropyl-N-methylaminopropyl)-9-hydroxyfluorene in 20 ml. of ethanol containing 1.1 g. of methyliodide was stirred at ambient temperature for thirty minutes. The precipitated solid was collected by filtration and recrystallized from fresh ethanol to afford 2.5 g. of 9-(3-N-isopropyl-N-methylaminopropyl)-9-hydroxyfluorene methiodide. M.P. 217°–219° C.

Analysis calc for $C_{21}H_{28}NOI$: Theory: C, 57.67; H, 6.45; N, 3.20. Found: C, 57.65; H, 6.30; N, 3.22.

EXAMPLE 17

Following the procedure of Example 16, 9-(3-N-isopropyl-N-methylaminopropyl)-9-aminocarbonylfluorene was reacted with allyl bromide in dichloromethane to give the corresponding quaternary ammonium salt, namely 9-(3-N-allyl-N-isopropylaminopropyl)-9-aminocarbonylfluorene methyl bromide.

EXAMPLE 18

9-(4-N-ethyl-N-Isopropylaminobutyl)-9-ethylaminocarbonylfluorene

To a stirred solution of 9-(4-N-ethyl-N-isopropylaminobutyl)-9-hydroxycarbonylfluorene in benzene is added oxalyl chloride. The reaction mixture is stirred for several hours and then the solvent is evaporated to give 9-(4-N-ethyl-N-isopropylaminobutyl)-9-chlorocarbonylfluorene as an oil. The oil thus formed is dissolved in dichloromethane containing triethylamine and stirred while ethylamine is added in one portion. After stirring the reaction mixture several hours, the solvent is removed to provide the corresponding N-alkyl amide, namely 9-(4-N-ethyl-N-isopropylaminobutyl)-9-ethylaminocarbonylfluorene.

EXAMPLE 19

9-(4-n-Propylaminobutyl)-9-aminocarbonylfluorene

A solution of 9-(4-aminobutyl)-9-aminocarbonylfluorene in benzene containing one equivalent of n-propyl bromide and triethylamine is stirred for several hours. Removal of the reaction solvent and distillation of the product affords 9-(4-n-propylaminobutyl)-9-aminocarbonylfluorene.

EXAMPLE 20

9-[3-(2,6-Dimethylpiperidino)propyl]-9-cyanofluorene 2,6-Dimethyl-1-(3-chloropropyl)piperidine was prepared by first reacting 169.5 g. of 2,6-dimethylpiperidine with 195.0 g. of 3-bromopropanol in 800 ml. of dry tetrahydrofuran to give 95.2 g. of 2,6-dimethyl-1-(3-hydroxypropyl)piperidine, and then chlorinating the latter compound by reaction with 178.5 g. of thionyl chloride in chloroform. The 2,6-dimethyl-1-(3-chloropropyl)piperidine was a crystalline solid melting at 169°–171° C.

A solution of 19.1 g. of 9-cyanofluorene in 500 ml. of dry toluene containing 4.7 g. of sodium amide was heated at reflux for two hours. After cooling the mixture to about 30° C., a solution of 27.1 g. of 2,6-dimethyl-1-(3-chloropropyl)piperidine in 100 ml. of dry toluene was added dropwise over ten minutes. The reaction mixture was again heated to reflux and stirred at that temperature for sixteen hours. The product was isolated by first cooling the reaction mixture to room temperature and then adding water dropwise to decompose any unreacted sodium amide. Additional water was added to the reaction mixture, and then the product was extracted therefrom into diethyl ether. The etheral extracts were combined, washed with water, dried, and the solvent was removed by evaporation under reduced pressure to afford a solid. The solid was crystallized from Skelly B to give 22.2 g. of 9-[3-(2,6-dimethylpiperidino)propyl]-9-cyanofluorene. M.P. 78°–81° C.

EXAMPLE 21

9-[3-(2,6-Dimethylpiperidino)propyl]-9-aminocarbonylfluorene, maleic acid salt

Twenty grams of concentrated sulfuric acid (90%) were cooled to 5° C. and slowly added to 5.0 g. of 9-[3-(2,6-dimethylpiperidine)propyl]-9-cyanofluorene. The reaction mixture was heated at 90° C. for forty-five minutes, and then was added in one portion to 50 g. of ice. The aqueous acid mixture was made alkaline by the addition of 10% aqueous sodium hydroxide, and the aqueous alkaline solution was extracted several times with ethyl acetate and diethyl ether. The organic extracts were combined, washed with water, dried, and the solvent was removed by evaporation under reduced pressure to provide 5.4 g. of 9-[3-(2,6-dimethylpiperidino)propyl]-9-aminocarbonylfluorene as a gum. The gum thus formed was dissolved in 150 ml. of ethyl acetate and 25 ml. of ethanol, to which was added 1.7 g.

of maleic acid. The crystalline precipitate which formed was collected by filtration and air dried to provide 1.3 g. of 9-[3-(2,6-dimethylpiperidino)propyl]-9-aminocarbonylfluorene, maleic acid salt. M.P. 182°–184° C.

Analysis calc. for $C_{28}H_{34}N_2O_5$: Theory: C, 70.27; H, 7.16; N, 5.85. Found: C, 69.98; H, 6.95; N, 5.70.

EXAMPLE 22

By following the procedure of Example 21, 5.0 g. of 9-(3-morpholinopropyl)-9-cyanofluorene (from Example 13) were reacted with 18.0 g. of concentrated sulfuric acid to provide, after salt formation and crystallization from ethanol and diethyl ether, 3.3 g. of 9-(3-morpholinopropyl)-9-aminocarbonylfluorene hydrochloride. M.P. 241°–243° C.

Analysis calc. for $C_{21}H_{25}ClN_2O_2$: Theory: C, 67.64; H, 6.76; N, 7.51. Found: C, 67.36; H, 6.51; N, 7.40.

EXAMPLE 23

9-(3-N-Benzyl-N-isopropylaminopropyl)-9-ethoxycarbonylfluorene

A solution of 14.7 g. of 9-(3-N-benzyl-N-isopropylaminopropyl)fluorene in 2000 ml. of dimethylsulfoxide containing 1.96 g. of sodium hydride was stirred at 17° C. for two hours. The reaction mixture was then diluted by the dropwise addition of 4.42 g. of ethyl chloroformate in 50 ml. of dimethylsulfoxide. Following the addition, the reaction mixture was stirred for two hours at 17° C., and then allowed to warm to room temperature, where stirring was continued for an additional sixteen hours. The reaction mixture next was added to 200 ml. of water containing 100 ml. of brine, and the aqueous mixture was extracted several times with diethyl ether. The ethereal extracts were combined, washed with after, dried, and the solvent was removed by evaporation to give, following distillation, 25.1 g. of 9-(3-N-benzyl-N-isopropylaminopropyl)-9-ethoxycarbonylfluorene, B.P. 237° C. at 0.3 torr.

Analysis calc. for $C_{29}H_{33}NO_2$: Theory: C, 80.96; H, 7.95; N, 3.37. Found: C, 80.96; H, 7.35; N, 3.42.

EXAMPLE 24

9-(3-Isopropylaminopropyl)-9-ethoxycarbonylfluorene

A solution of 9.6 g. of 9-(3-N-benzyl-N-isopropylaminopropyl)-9-ethoxycarbonylfluorene was hydrogenated in the presence of 2.0 g. of five percent palladium on charcoal according to the procedure of Example 14 to give, following isolation and crystallization from diethyl ether and ethanol, 2.3 g. of 9-(3-isopropylaminopropyl)-9-ethoxycarbonylfluorene. M.P. 177°–179° C.

Analysis calc. for $C_{22}H_{27}NO_2$: Theory: C, 70.67; H, 7.55; N, 3.75. Found: C, 70.44; H, 7.53; N, 3.50.

EXAMPLE 25

| Tablet | Mg. |
|---|---|
| 9-(3-isopropylaminopropyl)-9-aminocarbonylfluorene, hydrochloride | 200 |
| starch | 275 |
| sucrose | 225 |
| | 700 |

The above ingredients were thoroughly mixed with a lubricant and the mixture molded into tablets, each containing 20 mg. of active ingredient. Such tablets are administered orally as needed to a subject in need of antiarrhythmic treatment.

EXAMPLE 26

Formulation suitable for intravenous administration.

| Ingredient | |
|---|---|
| 9-(3-isopropylaminopropyl)-9-aminocarbonylfluorene, hydrochloride | 225 mg. |
| isotonic saline | 450 ml. |
| 10% aqueous glucose | 450 ml. |

The above ingredients were mixed to form a solution capable of being infused into a subject suffering from an arrhythmia.

EXAMPLE 27

9-(3-Isopropylaminopropyl)-9-aminocarbonylfluorene hydrochloride (a)

Preparation of 9-fluorene carboxylic acid

To a stirred cold (−10° C.) solution of 1200 g. of fluorene in 6.7 liters of tetrahydrofuran were added dropwise over 2 hours 8 moles of n-butyl lithium in 3 liters of hexane. The temperature was maintained below 5° C. during the addition. Following complete addition, the reaction mixture was warmed to room temperature and diluted with 6 gallons of toluene, followed by the slow addition of 24 liters of dry ice ($CO_2$). The reaction mixture was stirred for sixteen hours at room temperature, and then was further diluted with water. The organic layer was separated and then extracted several times with 1N sodium hydroxide. The aqueous alkaline extracts were combined, washed with diethyl ether, and then acidified with concentrated hydrochloric acid. The precipitate which formed was collected by filtration, washed with water and air dried at 55° C. to provide 1316 g. of 9-fluorene carboxylic acid. 87% yield. m.p. 224°–226° C.

Analysis calc. for $C_{14}H_{10}O_2$: Theory: C, 79.98; H, 4.79. Found: C, 79.74; H, 4.93.

(b)

Preparation of 9-aminocarbonylfluorene

A mixture of 2409 g. of 9-fluorene carboxylic acid and 3.8 liters of thionylchloride in 3.8 liters of carbon tetrachloride was heated at reflux for one hour. The mixture was cooled to room temperature and the solvent was removed by evaporation under reduced pressure to provide a solid. The solid thus formed was dissolved in 3.8 liters of acetone, and the solution was added portion-wise to a stirred solution of 32 liters of concentrated aqueous ammonium hydroxide. Following the addition, the precipitate which had formed was collected by filtration and crystallized from isopropanol to give 1588 g. of 9-aminocarbonyl fluorene. 66% yield. m.p. 250° C.

Analysis calc. for $C_{14}H_{11}NO$: Theory: C, 80.36; H, 5.30; N, 6.69. Found: C, 80.10; H, 5.27; N, 6.45.

(c)

Preparation of 9-aminocarbonyl-9-(2-cyanoethyl)fluorene

To a stirred suspension of 100 g. of 9-aminocarbonylfluorene in 3.3 liters of tetrahydrofuran was added in one portion 10 ml. of a 40% methanolic solution of benzyltrimethylammonium hydroxide (Triton B). The mixture was heated at 45° C. for 15 minutes, and then 26.2 g. of acrylonitrile was added to the reaction mixture in one portion. The reaction mixture then was heated at reflux for three hours. After cooling the solution to room temperature, the reaction solvent was removed by evaporation under reduced pressure. The solid residue was dissolved in ethyl acetate, washed several times with water, dried, and the solvent was removed by evaporation. The solid which was recovered was crystallized from dichloromethane and Skelly-B to provide 110 g. of 9-aminocarbonyl-9-(2-cyanoethyl)fluorene. Yield 87%. m.p. 148°–152° C.

Analysis calc. for $C_{17}H_{14}N_2O$: Theory: C, 77.84; H, 5.38; N, 10.68. Found: C, 78.74; H, 5.44; N, 9.58.

(d)

9-(3-Isopropylaminopropyl)-9-aminocarbonylfluorene hydrochloride

A mixture of 500 g. of 9-aminocarbonyl-9-(2-cyanoethyl)fluorene, 1500 ml. of isopropylamine and 100 g. of 5% palladium on carbon was placed in a one gallon high pressure hydrogenation bomb. The bomb was pressurized with hydrogen to a pressure of 1500 psi, and the reaction mixture was then stirred at 100° C. for ten hours, and for an additional eight hours at room temperature. The reaction mixture was filtered to remove the hydrogenation catalyst, and the solvent was removed from the filtrate by evaporation under reduced pressure. The residue was dissolved in ethyl acetate, and the solution was extracted several times with 1N hydrochloric acid. The acidic extracts were combined, made alkaline by the addition of sodium hydroxide, and the alkaline mixture was extracted with fresh ethyl acetate. The organic layer was separated, washed with water and dried. Removal of the solvent by evaporation under reduced pressure provided 9-(3-isopropylaminopropyl)-9-aminocarbonylfluorene as a solid residue. The solid was dissolved in methanol and treated with anhydrous hydrogen chloride. The crystalline product which formed was recrystallized from chloroform to afford 391 g. of 9-(3-isopropylaminopropyl)-9-aminocarbonylfluorene hydrochloride. Yield 60%. m.p. 216.5°–217° C.

Analysis calc. for $C_{20}H_{25}ClN_2O$: Theory: C, 69.65; H, 7.31; N, 8.12; Cl, 10.28. Found: C, 69.73; H, 7.02; N, 8.42; Cl. 10.38.

EXAMPLE 28

Following the procedure of Example 27, 27.98 g. of 9-(N,N-dimethylaminocarbonyl)fluorene were reacted with 10 ml. of Triton B and 7.95 g. of acrylonitrile to provide 13.0 g. of 9-(N,N-dimethylaminocarbonyl)-9-(2-cyanoethyl)fluorene. m.p. 109°–110° C.

Analysis calc. for $C_{19}H_{18}N_2O$: Theory: C, 78.59; H, 6.25; N, 9.65. Found: C, 78.31; H, 6.51; N, 9.35.

The product thus obtained was reacted with 115 ml. of isopropylamine in the presence of 3.0 g. of 5% palladium on carbon under a hydrogen pressure of 1500 psi. The reaction was carried out at 100° C. for ten hours. After normal workup and conversion of the product to the hydrochloride salt there was obtained 8.9 g. of 9-(3-isopropylaminopropyl)-9-(N,N-dimethylaminocarbonyl)fluorene. m.p. 170°–171° C.

Analysis calc. for $C_{22}H_{29}ClN_2O$: Theory: C, 70.85; H, 7.84; N, 7.51. Found: C, 70.59; H, 7.60; N, 7.34.

EXAMPLE 29

9-(3-Aminopropyl)-9-aminocarbonylfluorene

A 3.3 g. portion of 9-aminocarbonyl-9-(2-cyanoethyl)fluorene from Example 27 was hydrogenated in 95 ml. of glacial acetic acid under 4 atmospheres of hydrogen pressure for two hours at 24° C. in the presence of 1.5 g. of platinum oxide catalyst. The reaction mixture was filtered to remove the catalyst and the solvent was removed by evaporation under reduced pressure. The product which remained was dissolved in ethyl acetate and then extracted into 1N hydrochloric acid. The aqueous acid layer was separated, made alkaline with 50% sodium hydroxide, and extracted several times with fresh ethyl acetate. The extracts were combined, washed with water and with brine, dried, and the solvent was removed by evaporation under reduced pressure to provide 2.3 g. of a white solid. The solid was dissolved in 1N hydrochloric acid, filtered, and diluted with water to 100 ml. The aqueous acid solution was lyophilized to provide a white solid, which when crystallized from methanol and ethyl acetate was identified as 1.0 g. of 9-(3-aminopropyl)-9-aminocarbonylfluorene. m.p. 198°–200° C.

EXAMPLE 30

9-(3-Isopropylaminopropyl)-9-aminocarbonylfluoroene

A solution of 6.7 g. of 9-(3-aminopropyl)-9-aminocarbonylfluorene (prepared as described in Example 29) in 90 ml. of ethanol containing 1.6 g. of acetone was stirred at 40° C. for sixteen hours. The reaction mixture was then hydrogenated for two hours at ambient temperature in the presence of 2.0 g. of 5% palladium on carbon and hydrogen at a pressure of 60 psi. The reaction mixture next was filtered and the solvent was removed from the filtrate by evaporation to provide a foam. The foam was dissolved in ethyl acetate and then extracted into 1N hydrochloric acid. The aqueous acid layer was separated, made alkaline with 50% sodium hydroxide, and the product was extracted into fresh ethyl acetate. The organic extracts were combined, washed with water, dried, and the solvent was removed by evaporation under reduced pressure to provide 9-(3-isopropylaminopropyl)-9-aminocarbonylfluorene identical to that obtained in Example 27.

We claim:
1. A compound of the formula

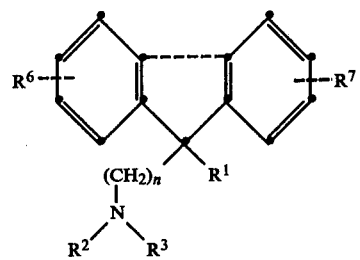

wherein:
$R^1$ is hydroxy, cyano, or $CONR^4R^5$ in which $R^4$ and $R^5$ independently are hydrogen or $C_1$–$C_6$ alkyl;

$R^2$ and $R^3$ independently are hydrogen, $C_1$-$C_6$ alkyl, $CH_2C_2$-$C_5$ alkenyl, phenyl-$C_1$-$C_3$ alkyl, or taken together with the nitrogen to which they are attached are a cyclic group of the formula

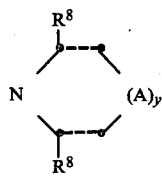

in which $R^8$ is hydrogen or $C_1$-$C_4$ alkyl; A is $CH_2$, O or NH; and y is zero or one; provided that $R^2$ is hydrogen when $R^1$ is hydroxy;
n is 3, 4 or 5;
$R^6$ and $R^7$ independently are hydrogen, $C_1$-$C_4$ alkyl or halogen,
and the pharmaceutically acceptable salts thereof.

2. The compound of claim 1 wherein:
$R^1$ is hydroxy, cyano, or $CONR^4R^5$ in which $R^4$ and $R^5$ independently are hydrogen or $C_1$-$C_6$ alkyl;
n is 3 or 4;
$R^2$ and $R^3$ independently are hydrogen, $C_1$-$C_6$ alkyl, $CH_2C_2$-$C_5$ alkenyl, phenyl-$C_1$-$C_3$ alkyl, or taken together are $C_4$-$C_5$ alkylene or —$CH_2CH_2$—O—$CH_2CH_2$—;
$R^6$ and $R^7$ are hydrogen;
and the pharmaceutically acceptable acid addition salts and lower alkyl quaternary ammonium salts thereof.

3. The compound of claim 2 wherein $R^1$ is hydroxy, $R^2$ is hydrogen and $R^3$ is $C_1$-$C_6$ alkyl.

4. The compound of claim 3 wherein $R^3$ is $C_1$-$C_3$ alkyl.

5. The compound of claim 4 wherein $R^3$ is methyl.

6. The compound of claim 4 wherein $R^3$ is ethyl.

7. The compound of claim 4 wherein $R^3$ is n-propyl.

8. The compound of claim 4 wherein $R^3$ is iso-propyl.

9. The compound of claim 1 wherein $R^1$ is cyano.

10. The compound of claim 9 wherein $R^3$ is $C_1$-$C_6$ alkyl.

11. The compound of claim 10 wherein $R^3$ is $C_1$-$C_3$ alkyl.

12. The compound of claim 11 wherein $R^3$ is iso-propyl.

13. The compound of claim 1 wherein $R^1$ is $CONR^4R^5$.

14. The compound of claim 13 wherein $R^4$ and $R^5$ both are hydrogen.

15. The compound of claim 14 wherein $R^6$ and $R^7$ both are hydrogen.

16. The compound of claim 15 wherein $R^3$ is $C_1$-$C_6$ alkyl.

17. The compound of claim 16 wherein $R^2$ is hydrogen.

18. The compound of claim 17 wherein $R^3$ is $C_1$-$C_3$ alkyl.

19. The compound of claim 18 wherein n is 3.

20. The compound of claim 19 wherein $R^3$ is methyl or ethyl.

21. The compound of claim 19 wherein $R^3$ is n-propyl.

22. The compound of claim 18 wherein $R^3$ is iso-propyl.

23. The compound of claim 22, said compound being 9-(3-isopropylaminopropyl)-9-aminocarbonylfluorene.

24. The compound of claim 1 as a pharmaceutically acceptable acid addition salt.

25. The compound of claim 24, said compound being 9-(3-isopropylaminopropyl)-9-aminocarbonylfluorene hydrochloride.

26. The compound of claim 24, said compound being 9-(3-isopropylaminopropyl)-9-aminocarbonylfluorene hydrobromide.

27. The compound of claim 1 as a $C_1$-$C_6$ alkyl quaternary ammonium salt.

28. The compound of claim 1 wheren n is 4.

29. The compound of claim 1 wheren n is 5.

* * * * *

UNITED STATES PATENT AND TRADEMARK OFFICE

CERTIFICATE EXTENDING PATENT TERM
UNDER 35 U.S.C. 156

Patent No.    : 4,452,745

Dated         : June 5, 1984

Inventor(s)   : William B. Lacefield et al

Patent Owner  : Eli Lilly and Company

This is to certify that there has been presented to the

COMMISSIONER OF PATENTS AND TRADEMARKS an application under 35 U.S.C. 156 for an extension of the patent term. Since it appears that the requirements of the law have been met, this certificate extends the term of the patent for the period of

2 YEARS with all rights pertaining thereto as provided by 35 USC 156 (b).

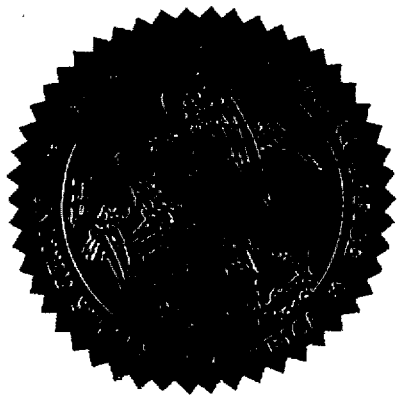

I have caused the seal of the Patent and Trademark Office to be affixed this 7th day of December 1990.

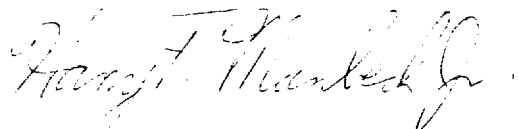

Harry F. Manbeck, Jr.
Assistant Secretary and Commissioner
 of Patents and Trademarks